US011459574B2

(12) United States Patent
Inui et al.

(10) Patent No.: US 11,459,574 B2
(45) Date of Patent: Oct. 4, 2022

(54) TRANSFORMANT HAVING ENTNER-DOUDOROFF PATHWAY AND PRODUCTION METHOD FOR ORGANIC COMPOUND USING SAME

(71) Applicant: RESEARCH INSTITUTE OF INNOVATIVE TECHNOLOGY FOR THE EARTH, Kyoto (JP)

(72) Inventors: Masayuki Inui, Kyoto (JP); Masako Suda, Kyoto (JP); Naoto Kato, Kyoto (JP); Satoshi Hasegawa, Kyoto (JP); Takahisa Kogure, Kyoto (JP); Toru Jojima, Nara (JP)

(73) Assignee: RESEARCH INSTITUTE OF INNOVATIVE TECHNOLOGY FOR THE EARTH, Kyoto (JP)

( * ) Notice: Subject to any disclaimer, the term of this patent is extended or adjusted under 35 U.S.C. 154(b) by 0 days.

(21) Appl. No.: 17/051,832

(22) PCT Filed: Mar. 27, 2019

(86) PCT No.: PCT/JP2019/013368
§ 371 (c)(1),
(2) Date: Oct. 30, 2020

(87) PCT Pub. No.: WO2019/211958
PCT Pub. Date: Nov. 7, 2019

(65) Prior Publication Data
US 2021/0054386 A1  Feb. 25, 2021

(30) Foreign Application Priority Data
May 1, 2018 (JP) .............................. JP2018-088425

(51) Int. Cl.
C12N 15/77 (2006.01)
C12P 7/40 (2006.01)

(52) U.S. Cl.
CPC ............... C12N 15/77 (2013.01); C12P 7/40 (2013.01)

(58) Field of Classification Search
None
See application file for complete search history.

(56) References Cited

U.S. PATENT DOCUMENTS 5,786,186 A    7/1998  Lancashire et al.
2003/0219882 A1 11/2003 Hara et al.
2010/0120105 A1  5/2010  Anthony et al.
2012/0184020 A1  7/2012  Picataggio et al.
2017/0268023 A1  9/2017  Amagai et al.

FOREIGN PATENT DOCUMENTS

EP       1 352 966         10/2003
EP       1352966 A2   *   10/2003  ............... C12N 9/88
JP       9-510360          10/1997
JP       2003-274988        9/2003
JP       3932945            6/2007
WO       2011/006136        1/2011
WO       2016/093294        6/2016

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Inui et al. J Mol Microbiol Biotechnol. 2004;8(4):243-54. (Year: 2004).*
International Search Report (ISR) dated Jun. 25, 2019 in International (PCT) Application No. PCT/JP2019/013368.
Yota Tsuge et al., "Metabolic engineering of Corynebacterium glutamicum for hyperproduction of polymer-grade L- and D-lactic acid", Applied Microbiology Biotechnology, vol. 103, Issue 8, pp. 3381-3391, Mar. 15, 2019.
Extended European Search Report dated Feb. 18, 2022 in corresponding European Patent Application No. 19796243.4.
Masayuki Inui et al., "Metabolic Engineering of Corynebacterium glutamicum for Fuel Ethanol Production under Oxygen-Deprivation Conditions", Journal of Molecular Microbiology and Biotechnology, 2004, 8, pp. 243-254.

* cited by examiner

Primary Examiner — Christian L Fronda
(74) Attorney, Agent, or Firm — Wenderoth, Lind & Ponack, L.L.P.

(57) ABSTRACT

Provided is a method for improving productivity in producing an organic compound in a bacterium that originally does not have an inherent ED pathway. In one aspect, provided is a transformant of a coryneform bacterium that is obtained by introducing the Entner-Doudoroff pathway into the coryneform bacterium as a host. In another aspect, provided is a transformant of a coryneform bacterium that is obtained by introducing, into a coryneform bacterium as a host a gene in which an enzyme having glucose-6-phosphate dehydrogenase activity is encoded, a gene in which an enzyme having 6-phosphogluconate dehydratase activity is encoded, and a gene in which an enzyme having 2-keto-3-deoxy-6-phosphogluconate aldolase activity is encoded.

11 Claims, No Drawings
Specification includes a Sequence Listing.

SEQUENCE LISTING

```
<160> NUMBER OF SEQ ID NOS: 14

<210> SEQ ID NO 1
<211> LENGTH: 3274
<212> TYPE: DNA
<213> ORGANISM: Zymomonas mobilis

<400> SEQUENCE: 1
atgacaaata ccgtttcgac gatgatattg tttggctcga ctggcgacct ttcacagcgt      60
atgctgttgc cgtcgcttta tggtcttgat gccgatggtt tgcttgcaga tgatctgcgt     120
atcgtctgca cctctcgtag cgaatacgac acagatggtt tccgtgattt tgcagaaaaa     180
gctttagatc gctttgtcgc ttctgaccgg ttaaatgatg acgctaaagc taaattcctt     240
aacaagcttt tctacgcgac ggtcgatatt acggatccga cccaattcgg aaaattagct     300
gacctttgtg gcccggtcga aaaaggtatc gccatttatc tttcgactgc gccttctttg     360
tttgaagggg caatcgctgg cctgaaacag gctggtctga ctggtccaac ttctcgcctg     420
gcgcttgaaa aacctttagg tcaagatctt gcttcttccg atcatattaa tgatgcggtt     480
ttgaaagttt tctctgaaaa gcaagtttat cgtattgacc attatctggg taaagaaacg     540
gttcagaatc ttctgaccct gcgttttggt aatgctttgt ttgaaccgct ttggaattca     600
aaaggcattg accacgttca gatcagcgtt gctgaaacgg ttggtcttga aggtcgtatc     660
ggttatttcg acggttctgg cagcttgcgc gatatggttc aaagccatat ccttcagttg     720
gtcgctttgg ttgcaatgga accaccggct catatggaag ccaacgctgt tcgtgacgaa     780
aaggtaaaag ttttccgcgc tctgcgtccg atcaataacg acaccgtctt tacgcatacc     840
```

```
gttaccggtc aatatggtgc cggtgtttct ggtggtaaag aagttgccgg ttacattgac      900
gaactgggtc agccttccga taccgaaacc tttgttgcta tcaaagcgca tgttgataac      960
tggcgttggc agggtgttcc gttctatatc cgcactggta agcgtttacc tgcacgtcgt     1020
tctgaaatcg tggttcagtt taaacctgtt ccgcattcga ttttctcttc ttcaggtggt     1080
atcttgcagc cgaacaagct gcgtattgtc ttacagcctg atgaaaccat ccagatttct     1140
atgatggtga agaaccggg tcttgaccgt aacggtgcgc atatgcgtga agttggctg       1200 gatctttccc tcacggatgt gtttaaagac cgtaaacgtc gtatcgctta tgaacgcctg     1260
atgcttgatc ttatcgaagg cgatgctact ttatttgtgc gtcgtgacga agttgaggcg     1320
cagtgggttt ggattgacgg aattcgtgaa ggctggaaag ccaacagtat gaagccaaaa     1380
acctatgtct ctggtacatg ggggccttca actgctatag ctctggccga acgtgatgga     1440
gtaacttggt atgactgatc tgcattcaac ggtagaaaag gttaccgcgc gcgttattga     1500
acgctcgcgg gaaacccgta aggcttatct ggatttgatc cagtatgagc gggaaaaagg     1560
cgtagaccgt ccaaacctgt cctgtagtaa ccttgctcat ggctttgcgg ctatgaatgg     1620
tgacaagcca gctttgcgcg acttcaaccg catgaatatc ggcgtcgtga cttcctacaa     1680
cgatatgttg tcggctcatg aaccatatta tcgctatccg gagcagatga agtatttgc     1740 tcgcgaagtt ggcgcaacgg ttcaggtcgc cggtggcgtg cctgctatgt gcgatggtgt     1800
gacccaaggt cagccgggca tggaagaatc cctgtttagc cgcgatgtta tcgctttggc     1860
taccagcgtt tctttgtctc atggtatgtt tgaaggggct gcccttctcg gtatctgtga     1920
caagattgtc cctggtctgt tgatgggcgc tctgcgcttt ggtcacctgc cgaccattct     1980
ggtcccatca ggcccgatga cgactggtat cccgaacaaa gaaaaaatcc gtatccgtca     2040
gctctatgct cagggtaaaa tcggccagaa agaacttctg gatatggaag cggcttgcta     2100
ccatgctgaa ggtacctgca ccttctatgg tacggcaaac accaaccaga tggttatgga     2160
agtcctcggt cttcatatgc caggttcggc atttgttacc ccgggtaccc cgctccgcca     2220
ggctctgacc cgtgctgctg tgcatcgcgt tgctgaattg ggttggaagg gcgacgatta     2280
tcgtccgctt ggtaaaatca ttgacgaaaa atcaatcgtc aatgctattg ttggtctgtt     2340
ggcaaccggt ggttccacca accataccat gcatattccg gccattgctc gtgctgctgg     2400
tgttatcgtt aactgaatg acttccatga tctttctgaa gttgttccgt tgattgcccg      2460
catttacccg aatggcccgc gcgacatcaa tgaattccag aatgcaggcg gcatggctta    2520
tgtcatcaaa gaactgcttt ctgctaatct gttgaaccgt gatgtcacga ccattgccaa    2580
gggcggtatc gaagaatacg ccaaggctcc ggcattaaat gatgctggcg aattggtctg    2640
gaagccagct ggcgaacctg gtgatgacac cattctgcgt ccggttccta atcctttcgc    2700
aaaagatggc ggtctgcgtc tcttggaagg taaccttggc cgtgcaatgt acaaggccag    2760
tgcggttgat cctaaattct ggaccattga agcaccggtt cgcgtcttct ctgaccaaga    2820
cgatgttcag aaagccttca aggctggcga attgaacaaa gacgttatcg ttgttgttcg    2880
tttccagggc ccgcgcgcaa acggtatgcc tgaattgcat aagctgaccc cggctttggg    2940
tgttctgcag gataatggct acaaagttgc tttggtaact gatggtcgta tgtccggtgc    3000
taccggtaaa gttccggttg ctttgcatgt cagcccagaa gctcttggcg tggtgccat     3060 cggtaaatta cgtgatggcg atatcgtccg tatctcggtt gaagaaggca aacttgaagc    3120
tttggttcca gctgatgagt ggaatgctcg tccgcatgct gaaaaaccgg ctttccgtcc    3180
```

```
gggaaccgga cgcgaattgt ttgatatctt ccgtcagaat gctgctaaag ctgaagacgg    3240
tgcagtcgca atatatgcag gtgccggtat ctaa                                3274

<210> SEQ ID NO 2
<211> LENGTH: 627
<212> TYPE: DNA
<213> ORGANISM: Zymomonas mobilis

<400> SEQUENCE: 2
atgcgtgata tcgattccgt aatgcgtttg gcaccggtta tgccggtcct cgtcattgaa      60
gatattgctg atgcaaaacc tatcgcagaa gctttggttg ctggtggtct gaacgttctt     120
gaagtaacgc ttcgcacccc ttgtgctctt gaagccatca agatcatgaa agaagttccg     180
ggtgccgttg ttggtgccgg tacggttctg aacgcaaaaa tgctcgacca agctcaggaa     240
gctggttgcg aattttcgt tagcccgggt ctgaccgctg acctcggcaa gcatgctgtt     300
gcccagaaag cagctttgct tccaggtgtt gctaatgctg ctgatgtgat gcttggtctt     360
gaccttggtc ttgatcgctt caaattcttc ccggctgaaa atatcggtgg tttacctgcc     420
ctgaagtcca tggcttctgt tttccgtcag gttcgtttct gcccgaccgg cggtatcacc     480
ccgacgtcag ctcctaaata tcttgaaaac ccgtccattc tttgcgtcgg tggtagctgg     540
gttgttccgg ctggcaaacc agatgtcgca aaaatcacgg cactcgctaa gaagcttct      600 gctttcaagc gcgctgctgt tgcctaa                                        627

<210> SEQ ID NO 3
<211> LENGTH: 34
<212> TYPE: DNA
<213> ORGANISM: Artificial Sequence
<220> FEATURE:
<223> OTHER INFORMATION: Amplification Primer (F) for zwf-edd gene

<400> SEQUENCE: 3
ctctagtact atgacaaaata ccgtttcgac gatg                                34

<210> SEQ ID NO 4
<211> LENGTH: 30
<212> TYPE: DNA
<213> ORGANISM: Artificial Sequence
<220> FEATURE:
<223> OTHER INFORMATION: Amplification Primer (R) for zwf-edd gene

<400> SEQUENCE: 4
ctctagtact ttagataccg gcacctgcat                                      30

<210> SEQ ID NO 5
<211> LENGTH: 31
<212> TYPE: DNA
<213> ORGANISM: Artificial Sequence
<220> FEATURE:
<223> OTHER INFORMATION: Amplification Primer (F) for eda gene

<400> SEQUENCE: 5
ctctcatatg cgtgatatcg attccgtaat g                                    31

<210> SEQ ID NO 6
<211> LENGTH: 27
<212> TYPE: DNA
<213> ORGANISM: Artificial Sequence
<220> FEATURE:
<223> OTHER INFORMATION: Amplification Primer (R) for eda gene

<400> SEQUENCE: 6
```

-continued ctctcatatg ttaggcaaca gcagcgc                                           27

<210> SEQ ID NO 7
<211> LENGTH: 36
<212> TYPE: DNA
<213> ORGANISM: Artificial Sequence
<220> FEATURE:
<223> OTHER INFORMATION: Amplification Primer

<400> SEQUENCE: 7
ctcttctaga gtcgacggct gtgcaggtcg taaatc                                 36

<210> SEQ ID NO 8
<211> LENGTH: 37
<212> TYPE: DNA
<213> ORGANISM: Artificial Sequence
<220> FEATURE:
<223> OTHER INFORMATION: Amplification Primer

<400> SEQUENCE: 8
ctctgatatc aacacacctt tctaaaaagt ttccttc                                37

<210> SEQ ID NO 9
<211> LENGTH: 30
<212> TYPE: DNA
<213> ORGANISM: Artificial Sequence
<220> FEATURE:
<223> OTHER INFORMATION: Amplification Primer

<400> SEQUENCE: 9
ctcttctaga gctttgttag gtgtctctgg                                        30

<210> SEQ ID NO 10
<211> LENGTH: 30
<212> TYPE: DNA
<213> ORGANISM: Artificial Sequence
<220> FEATURE:
<223> OTHER INFORMATION: Amplification Primer

<400> SEQUENCE: 10
ctcttctaga tcaccaccat gaagaagtcc                                        30

<210> SEQ ID NO 11
<211> LENGTH: 30
<212> TYPE: DNA
<213> ORGANISM: Artificial Sequence
<220> FEATURE:
<223> OTHER INFORMATION: Amplification Primer

<400> SEQUENCE: 11
ctctctcgag gcaacagtgc ttcatactgc                                        30

<210> SEQ ID NO 12
<211> LENGTH: 29
<212> TYPE: DNA
<213> ORGANISM: Artificial Sequence
<220> FEATURE:
<223> OTHER INFORMATION: Amplification Primer

<400> SEQUENCE: 12
ctctctcgag acggattgaa cccaagacg                                         29

<210> SEQ ID NO 13
<211> LENGTH: 32
<212> TYPE: DNA

```
<213> ORGANISM: Artificial Sequence
<220> FEATURE:
<223> OTHER INFORMATION: Amplification Primer

<400> SEQUENCE: 13
ctctcctgca ggcacgaacc tcaattagcc tg                               32

<210> SEQ ID NO 14
<211> LENGTH: 32
<212> TYPE: DNA
<213> ORGANISM: Artificial Sequence
<220> FEATURE:
<223> OTHER INFORMATION: Amplification Primer

<400> SEQUENCE: 14
ctctcctgca gggatgactt gatgcaggtg tg                               32
```

TRANSFORMANT HAVING ENTNER-DOUDOROFF PATHWAY AND PRODUCTION METHOD FOR ORGANIC COMPOUND USING SAME

TECHNICAL FIELD

The present disclosure relates to a microorganism having enhanced ability for implementing a biorefinery process, and to a highly productive method for producing an organic compound using the same.

BACKGROUND ART

Producing organic compounds such as organic acids, amino adds, and alcohols from biomass-derived saccharides as raw materials by a biological method so as to produce chemical products and energy products is called biorefinery. On the other hand, producing these organic compounds from fossil resources is called petroleum refinery. Biorefinery, unlike petroleum refinery, solves problems such as resources exhaustion and global warming, and is expected to be an environmentally conscious manufacturing technique.

However, biorefinery is generally said to have lower productivity, as compared with petroleum refinery.

One of techniques for improving the productivity by the biological method is to improve the rate of metabolism of saccharides into various kinds of organic compounds and the yields thereof so as to improve the concentration of the organic compounds accumulated in a bio-reaction solution (to implement the separation and purification of a target organic compound at a high efficiency).

The saccharide metabolism by bacteria of the genus *Corynebacterium* is performed through the Embden-Meyerhof-Parnas pathway (EMP pathway), and the pentose phosphate pathway (PP pathway), wherein saccharides are converted into pyruvate, and thereafter, they are further converted into various types of organic compounds. On the other hand, some microorganisms such as *Zymomonas mobilis* metabolizes saccharides through the Entner-Doudnroff pathway (ED pathway).

The ED pathway is composed of glucose-6-phosphate dehydrogenase (hereinafter abbreviated as "G6DH") that converts glucose-6-phosphate into 6-phosphoglucono-1,5-lactone; 6-phosphogluconolactonase that converts 6-phosphoglucono-1,5'-lactone into 6-phosphogluconate; 6-phosphogluconate dehydratase (hereinafter abbreviated as "EDD") that catalyzes a reaction of conversion from 6-phosphogluconate into 2-keto-3-deoxy-6-phosphogluconate; and 2-keto-3-deoxy-6-phosphogluconate aldolase (hereinafter abbreviated as "EDA") as an enzyme that cleaves 2-keto-3-deoxy-6-phosphogluconate so as to produce glyceraldehyde-3-phosphate and pyruvate. It is said that the saccharide metabolism through the ED pathway has a low efficiency in the production of ATP, and to compensate it, the rate of saccharide metabolism through the ED pathway is greater than that through the EMP pathway; as a result, regarding the fermentative production, a high productivity can be achieved with microorganisms having the ED pathway.

Patent Document 1 relates to yeasts of the genus *Saccharomyces*, and discloses an example in which, by introducing the ED pathway into the yeasts modified so that saccharide metabolism cannot be performed through the EMP pathway the pathway for saccharide metabolism is modified so that saccharides are metabolized only through the ED pathway.

Patent Document 2 discloses an isobutanol producing technique in which *Escherichia coli* an yeast (*Saccharomyces cerevisiae*), or a lactic acid bacterium (*Lactobacillus plantarum*) is used as a host, and the ED pathway is introduced or strengthened therein, while enzymes of the EMP pathway and the PP pathway are inactivated so that only the carbon flux into the ED pathway is increased.

Patent Document 3 indicates that the reinforcement of an inherent ED pathway, more specifically, the reinforcement of 6-phosphogluconate dehydratase activity, or 2-keto-3-deoxy-6-phosphogluconate aldolase activity, or alternatively, both of these activities, improves the yield in the production of L-amino acid.

PRIOR ART DOCUMENT

Patent Document

Patent Document 1: JP-T-hei-9(1997)-510360
Patent Document 2: US Patent Publication No. 20100120105
Patent Document 3: JP3932945

SUMMARY OF THE INVENTION

Problem to be Solved by the Invention

The present disclosure, in one aspect, provides a method for improving productivity in producing an organic compound in a bacterium that originally does not have an inherent ED pathway.

Means to Solve the Problem

The present disclosure, in one aspect, relates to a transformant of a coryneform bacterium that is obtained by introducing the Entner-Doudoroff pathway into the coryneform bacterium as a host.

The present disclosure, in another aspect, relates to a transformant of a coryneform bacterium that is obtained by introducing, into a coryneform bacterium as a host, a gene in which an enzyme having glucose-6-phosphate dehydrogenase activity is encoded, a gene in which an enzyme having 6-phosphogluconate dehydratase activity is encoded, and a gene in which an enzyme having 2-keto-3-deoxy-6-phosphogluconate aldolase activity is encoded.

The present disclosure, in another aspect, relates to an organic compound producing method that includes the steps of causing the transformant of the coryneform bacterium according to the present disclosure to react in a reaction solution in which at least one of factors necessary for growth is removed, or in a reaction solution under reduction conditions; and collecting an organic compound in a reaction medium.

Effect of the Invention

According to the present disclosure, in one aspect, the production of an organic compound in a coryneform bacterium can be made efficient. For example, the production rate and/or yield in the production of an organic compound can be improved.

MODE FOR CARRYING OUT THE INVENTION

As a result of earnest studies, the present inventors found that the productivity in producing an organic compound can be improved by causing an enzyme gene that constitutes an Entner-Doudoroff pathway (ED pathway) to be expressed in a coryneform bacterium so that two glycolytic pathways of an Embden-Meyerhof-Parnas pathway (BMP pathway) and the ED pathway exist in combination in a coryneform bacterium.

It is estimated that, by causing the two glycolytic pathways of the ED pathway and the BMP pathway to function in a coryneform bacterium that, in a wild type, does not have the ED pathway, the rate of metabolism, conversion and consumption of saccharides is improved, whereby the productivity in producing an organic compound is improved. The present disclosure, however; is not limited to this mechanism.

According to the present disclosure, in one aspect, the conversion rate and/or conversion proportion (yield) of a carbon material into an organic compound as a metabolic product of a saccharide can be improved.

It should be noted that an inherent EMP pathway is inactivated in the configurations disclosed by Patent Documents 1 and 2.

Further, in the configuration disclosed by Patent Document 3, an inherent ED pathway is reinforced, but the amino add production rate is rather decreased by the reinforcement of the ED pathway.

[Host]

In the present disclosure, the host into which an ED pathway is introduced is a coryneform bacterium.

A coryneform bacterium, originally, in other words, in the wild type existing in nature, does not have an ED pathway.

In the present disclosure, the coryneform bacteria are a group of microorganisms defined in Bergey's Manual of Determinative Bacteriology, Vol. 8, 599 (1974), and are not particularly limited as long as they grow under normal aerobic conditions. The specific examples include bacteria of the genus *Corynebacterium*, bacteria of the genus *Brevibacterium*, bacteria of the genus *Arthrobacter*, bacteria of the genus *Mycobacterium*, and bacteria of the genus *Micrococcus*. Among the coryneform bacteria, bacteria of the genus *Corynebacterium* are preferred.

Examples of the genus *Corynebacterium* include *Corynebacterium glutamicum, Corynebacterium effidens, Corynebacterium ammoniagenes, Corynebacterium halotolerance,* and *Corynebacterium alkanolyticum*. Among them, *Corynebacterium glutamicum* is preferred for safety and high xylooligosaccharide utilization.

Examples of preferred strains include *Corynebacterium glutamicum*R (FERM P-18976), ATCC13032, ATCC13869, ATCC13058, ATCC13059, ATCC13060, ATCC13232, ATCC13286, ATCC13287, ATCC13655, ATCC13745, ATCC13746, ATCC13761, ATCC14020, ATCC31831, MJ-233 (PERM BP-1497), and MJ-233AB-41 (PERM BP-1498). Among them, strains R (PERM P-18976), ATCC13032, and ATCC13869 are preferred.

These strains are available from NBRC (NITE Biological Resource Center), ATCC (American Type Culture Collection), etc., which are microorganism culture collections.

Further, these microorganisms are not only wild strains that exist in the natural world, but may be mutant strains or gene recombinant strains of the same.

[Introduction of ED Pathway]

In one of exemplary forms of introduction of the ED pathway into a host coryneform bacterium, at least three genes indicated below are introduced:

(1) a gene in which an enzyme having glucose-6-phosphate dehydrogenase activity is encoded;
(2) a gene in which an enzyme having 6-phosphogluconate dehydratase activity is encoded; and
(3) a gene in which an enzyme having 2-keto-3-deoxy-6-phosphogluconate aldolase activity is encoded.

A gene used for the introduction of the ED pathway can be acquired from a variety of organisms; the origin of the same is not particularly limited, as long as the gene functions in the host coryneform bacterium. The gene sequence can be searched on a common gene sequence database (for example, KEGG; http://www.genome.jp/kegg/genes.html).

In a gene used for the introduction of the ED pathway, any amino acid may be deleted, added, or substituted in the amino acid sequence encoded by the gene, as long as the respective enzymes thereof have the above-described enzyme activities (1) to (3).

In the present disclosure, the introduction of the enzyme genes that constitute the ED pathway into a host coryneform bacterium can be performed by using a common gene recombination technique (for example, the method proposed by Michael R Green & Joseph Sambrook, "Molecular cloning", Cold spring Harbor Laboratory Press); it can be implemented in the form of the introduction of a gene by using a plasmid vector, or the incorporation of a gene into a host coryneform bacterium chromosome.

In the present disclosure, "incorporating/introducing a gene" means incorporating or introducing a gene in a host so that the gene can be expressed in the host, in one or a plurality of embodiments.

For example, to introduce the glucose-6-phosphate dehydrogenase gene into a host coryneform bacterium, it is preferable to incorporate an appropriate promoter in an upstream region on the 5' side of the gene, and it is more preferable to additionally incorporate a terminator in a downstream region on the 3' side.

[Enzyme Having Glucose-6-Phosphate Dehydrogenase Activity]

In the present disclosure, the "enzyme having glucose-6-phosphate dehydrogenase (G6DH) activity" means an enzyme having activity of converting glucose-6-phosphate into 6-phosphoglucono-1,5-lactone.

In the present disclosure, it is preferable that the enzyme having G6DH activity can use oxidized nicotinamide dinucleotide ($NAD^+$) as a coenzyme, with a view to making the organic compound production efficient.

Examples of the gene in which an enzyme using $NAD^+$ as a coenzyme and having glucose-6-phosphate dehydrogenase activity is encoded include a glucose-6-phosphate-1-dehydrogenase gene (zwf gene) of *Zymomonas mobilis*, and an ortholog of the same. Examples of the ortholog include orthologs of the genus *Escherichia*, the genus *Pseudomonas*, the genus *Enterobacter*, and the genus *Pantoea*.

It should be noted that the "ortholog gene" in the present disclosure means an analog gene that encodes a protein having a homologous function, existing in a different organism (for example, a different species, a different genus).

[Enzyme Having 6-Phosphogluconate Dehydratase Activity]

In the present disclosure, an "enzyme having 6-phosphogluconate dehydratase (EDD) activity" means an enzyme having an activity of catalyzing a reaction of conversion from 6-phosphogluconate into 2-keto-3-deoxy-6-phosphogluconate.

In the present disclosure, examples of the gene in which the enzyme having EDD activity is encoded include a 6-phosphogluconate dehydrogenase gene (edd gene) of *Zymomonas mobilis*, and an ortholog of the same. Examples of the ortholog include orthologs of the genus *Escherichia*, the genus *Pseudomonas*, the genus *Enterobacter*, and the genus *Pantoea*.

[Enzyme Having 2-Keto-3-Deoxy-6-Phosphogluconate Aldolase Activity]

In the present disclosure, an "enzyme having 2-keto-3-deoxy-6-phosphogluconate aldolase (EDA) activity" means an enzyme having an activity of cleaving 2-keto-3-deoxy 6-phosphogluconate to produce glyceraldehyde-3-phosphate and pyruvate.

In the present disclosure, examples of the gene in which the enzyme having EDA activity is encoded include a 6-phosphogluconate dehydratase gene (eda gene) of *Zymomonas mobilis*, and an ortholog of the same. Examples of the ortholog include orthologs of the genus *Escherichia*, the genus *Pseudomonas*, the genus *Enterobacter*, and the genus *Pantoea*.

[Transformant]

The present disclosure, in one aspect, relates to a transformant of a coryneform bacterium that is obtained by introducing the ED pathway into the coryneform bacterium as a host.

A transformant according to the present disclosure, in one or a plurality of embodiments, is a transformant of a coryneform bacterium that is obtained by introducing at least the above-described genes (1) to (3) into the coryneform bacterium as a host.

With the introduction of the ED path way into a host coryneform bacterium, the production of pyruvate and/or phosphoenolpyruvate in a cell is accelerated.

The transformant according to the present disclosure may be further characterized in that another gene (or genes) is introduced therein, or that a gene (or genes) is deleted and/or mutated, to produce an organic compound or to make the production more efficient. The above-described introduction and the like of a gene can be appropriately designed by a person skilled in the art, according to an organic compound to be produced.

[Organic Compound]

Examples of the organic compound produced by the transformant according to the present disclosure, in one or a plurality of embodiments, include a compound produced from pyruvate as an intermediate, and a compound produced from phosphoenolpyruvate as an intermediate.

Examples of the compound produced from pyruvate as an intermediate or the compound produced from phosphoenolpyruvate as an intermediate include at least one selected from the group consisting of monocarbaxylates, dicarboxylates, ketocarboxylates, hydroxycarboxylates, amino adds, monoalcohols, polyols, aromatic compounds, and vitamins.

Examples of the compound produced from pyruvate as an intermediate include L-lactate, D-lactate, acetate, 3-hydroxypropionate, acrylate, succinate, fumarate, malate, oxaloacetate, citrate, cis-aconitate, itaconate, isocitrate, 2-oxoglutarate, 2-hydroxyisovalerate, ethanol, 1,3-propanediol, glycerol, butanol, isobutanol, 1,4-butanediol, xylitol, sorbitol, valine, leucine, alanine, aspartate, lysine, isoleucine, and threonine.

Examples of the compound produced from phosphoenolpyruvate as an intermediate include shikimate, protocatechuate, catechol, 4-hydroxybenzoate, phenol, tyrosine, phenyl alanine, and tryptophan.

[Method for Producing Organic Compound]

The transformant according to the present disclosure, in a solution of a reaction without bacterial cell growth, can produce a compound produced from pyruvate as an intermediate or a compound produced from phosphoenolpyruvate as an intermediate, using saccharide as a raw material, at a high efficiency; examples of the produced compound include monocarboxylates, dicarboxylates, ketocarboxylates, hydroxycarboxylates, amino adds, monoalcohols, polyols, aromatic compounds, and vitamins.

Thus, the present disclosure, in another aspect, relates to an organic compound producing method that includes the steps of causing the transformant according to the present disclosure to react in a reaction solution in which at least one of factors necessary for growth is removed, or in a reaction solution under reduction conditions; and collecting an organic compound in a reaction medium.

In the organic compound producing method according to the present disclosure, first of all, the above-described transformant according to the present disclosure is cultured to grow under aerobic conditions.

The transformant according to the present disclosure can be cultured by using a normal nutrient medium that contains a carbon source, a nitrogen source, inorganic salts, and the like. In the culture, as a carbon source, for example, glucose, waste molasses, or the like can be used alone or in mixture, and as a nitrogen source, for example, ammonium, ammonium sulfate, ammonium chloride, ammonium nitrate, urea, or the like can be used alone or in mixture. Further, as an inorganic salt, for example, dibasic potassium phosphate, potassium dihydrogen phosphate, magnesium sulfate, or the like can be used. In addition to these, nutrients such as peptone, meat extract, yeast extract, cam steep liquor, casamino acid, and various types of vitamins such as biotin or thiamin can be appropriately added to the medium as required.

Generally, the culturing can be carried out under aerobic conditions such as aeration stirring or shaking, at a temperature of about 20° C. to about 60° C., preferably about 25° C. to about 35° C. The pH during the culturing is in a range of, for example, around 5 to 10, preferably around 7 to 8, and the pH adjustment during the culturing can be carried out by adding acid or alkali. The carbon source concentration at the start of the culturing is about 1% (W/V) to about 20% (W/V), preferably about 2% (W/V) to about 5% (W/V). Further, the culturing period is generally about 1 to 7 days.

Next, cultured bacterial cells of the transformant according to the present disclosure are collected A method for collecting and separating cultured bacterial cells from the cultured substance thus obtained as described above is not limited particularly, and a known method such as centrifugation or membrane separation can be used.

The cultured bacterial cells thus collected may be processed, and the processed bacterial cells thus obtained may be used in the next step. Examples of the processed bacterial cells include cultured bacterial cells subjected to a certain processing operation, for example, immobilized bacterial cells that are obtained by immobilizing bacterial cells with acrylamide, carrageenan, or the like.

In the organic compound production reaction by the cultured bacterial cells of the transformant according to the present disclosure, collected and separated from the cultured substance thus obtained as described above, or by the processed bacterial cells obtained from the same, any production process under aerobic conditions or reduction conditions may be used, as long as it is in a solution of a reaction without bacterial cell growth. The organic compound production process may be of a batch type, or of a continuous type.

In the present disclosure, "does not grow" includes "substantially does not grow", and "hardly grows". For example, in a reaction under aerobic conditions, growth of the transformant can be avoided or inhibited by the use of a reaction solution in which one or more of compounds essential for the growth of the microorganism, for example, vitamins, such as biotin and thiamine, nitrogen sources, etc. is depleted or limited.

Besides, under reducing conditions, coryneform bacteria substantially do not grow, and therefore, the composition of the reaction solution is not limited. The oxidation-reduction potential of the reaction solution under reducing conditions is preferably about −200 mV to about −500 mV, and more preferably about −150 mV to −500 mV. The reduced state of the reaction solution can be simply estimated using a resazurin indicator (in a reduced state, decolorization from blue to colorless is observed). However, for precise measurement, a redox-potential meter (for example, ORP Electrodes made by BROADLEY JAMES) may be used.

In the present disclosure, it is preferable that reducing conditions are maintained immediately after bacterial cells or processed bacterial cells are added to a reaction solution until an organic compound is collected; however, a reaction solution is in a reduced state at least at the point in time when an organic compound is collected. It is desirable that a reaction solution is kept under reducing conditions during about 50% or mere of a reaction period, preferably during about 70% or more of the same, and more preferably during about 90% or more of the same. Particularly, it is more desirable that a reaction solution has an oxidation-reduction potential kept at about −200 mV to about −500 mV during about 50% or more of a reaction period, preferably during about 70% or more of the same, and more preferably during about 90% or more of the same.

Thus, the present disclosure, in one aspect, relates to an organic compound producing method that includes the steps of causing a bacterium transformant according to the present disclosure to react in a reaction solution in which at least one of factors necessary far growth is removed, or in a reaction solution under reduction conditions; and collecting an organic compound in a reaction medium.

The reaction solution contains an organic carbon source (for example, saccharides) that are raw materials used in the production of an organic compound. Examples of the organic carbon source include materials that the transformant according to the present disclosure can utilize in a biochemical reaction.

Specifically examples of saccharides include monosaccharides, such as glucose, xylose, arabinose, galactose, fructose, and mannose; disaccharides, such as cellobiose, sucrose, lactose, and maltose; and polysaccharides, such as dextrin and soluble starch: etc. Among these, glucose is preferable.

Finally, the organic compound produced in the reaction medium as described above is collected. For doing so, a known method that is used in bioprocessing can be used. Examples of such a known method include the salting-out method, the recrystallization method, the organic solvent extraction method, the distillation method (reactive distillation by esterification etc.), the chromatography separation method, and the electrodialysis method, which can be used with respect to a solution of a produced organic compound. The method for separating and purifying a produced organic compound may be decided appropriately according to properties of the produced organic compound.

The present disclosure relates to the following, in one or a plurality of embodiments:

[1] A transformant of a coryneform bacterium that is obtained by introducing the Entner-Doudoroff pathway into the coryneform bacterium as a host.

[2] A transformant of a coryneform bacterium that is obtained by introducing, into the coryneform bacterium as a host:
a gene in which an enzyme having glucose-6-phosphate dehydrogenase activity is encoded;
a gene in which an enzyme having 6-phosphogluconate dehydratase activity is encoded; and
a gene in which an enzyme having 2-keto-3-deoxy-6-phosphogluconate aldolase activity is encoded.

[3] The transformant according to Item [2], wherein the glucose-6-phosphate dehydrogenase is an enzyme that can use oxidized niacinamide dinucleotide as a coenzyme.

[4] The transformant according to any one of Items [1] to [3], wherein the coryneform bacterium as a host is *Corynebacterium glutamicum*.

[5] The transformant according to any one of Items [1] to [4], obtained by further introducing a gene for improving efficiency in production of an organic compound.

[6] The transformant according to any one of Items [1] to (5), wherein the coryneform bacterium as a host is *Corynebacterium glutamicum* R (FERM P-18976), ATCC13032, or ATCC13869.

[7] A transformant of *Corynebacterium glutamicum* ALA98 (Accession Number: NITE BP-02688).

[8] An organic compound producing method including the steps of causing the transformant according to any one of Items [1] to [7] to react in a reaction solution in which at least one of factors necessary for growth is removed, or in a reaction solution under reduction conditions; and collecting an organic compound in a reaction medium.

[9] The organic compound producing method according to Item [8], wherein the steps include converting at least one saccharide selected from the group consisting of glucose, fructose, cellobiose, xylobiose, sucrose, lactose, maltose, dextrin, xylose, arabinose, galactose, mannose; and soluble starch, into the organic compound in the reaction solution by using the transformant according to any one of Items [1] to [7], and collecting the organic compound from the reaction solution.

[10] The organic compound producing method according to Item [8] or [9], wherein the organic compound is either a compound produced from pyruvate as an intermediate, or a compound produced from phosphoenolpyruvate as an intermediate.

[11] The organic compound producing method according to any one of Items [8] to [10], wherein the organic compound is at least one selected from the group consisting of monocarbaxylates, dicarboxylates, ketocarboxylates, hydroxycarboxylates, amino adds, monoalcohols, polyols, aromatic compounds, and vitamins.

EXAMPLE

The following description describes the present disclosure in detail, while referring to examples, but the present disclosure is not limited to these examples.

Example 1

Construction of Strain that Produces Ethanol Isobutanol, D-Lactate, Alanine, and Shikimate, Using ED Pathway-Introduced *Corynebacterium glutamicum* as Host (1) Preparation/Obtainment of Chromosomal DMA Chromosomal DNAs were prepared from the following strains.

*Corynebacterium glutamicum* R (FERM P-18976), and *Zymomonas mobilis* ATCC 31821 were cultured according to information obtained from organizations from which the strains are available, and thereafter, chromosomal DNAs thereof were prepared by using DNA genome extraction kit (trade name: "GenomicPrep Cells and Tissue DNA Isolation Kit", manufactured by Amersham PLC).

(2) Construction of Gene Expression Plasmid

Primer sequences used for isolating target enzyme genes are shown in Table 1. In PCR, Veriti Thermal Cycler (manufactured by Applied Biosystems Inc.) was used, and PrimeSTAR HS DNA Polymerase (manufactured by Takara Bio Inc.) was used as a reaction reagent DNA fragments obtained were introduced into cloning vectors containing tac promoter (pCRG5, pCRB214 (FEBS Lett. 2012 Nov. 30; 586(23): 4228-42321).

The names of the cloning vectors introduced and the plasmids obtained are shown in Table 2. Incidentally, since zwf and edd were arranged continuously in the same orientation cm the chromosome, they were cloned altogether (SEQ ID NO. 1).

Construction of pCRG5 Cloning Vector

A cloning vector pCRG5 was constructed by introducing a tac promotor sequence and a rrnB T1T2 bidirectional terminator sequence derived from a cloning vector pKK223-3 (manufactured by Pharmacia) into a vector pCRB22 [Appl Environ Microbiol 2012 June; 78(12): 4447-4457] including a pCASE1 ori sequence. To amplify the tac promoter sequence, primers of SEQ ID NOs. 7 and 8 were used, and the obtained DNA fragment was introduced into pCRB210 [Microbiology. 2015 February; 161 (Pt 2): 254-263/WO2012/033112]. The cloning vector including the tac promoter thus obtained was named pCRG5.

TABLE 1

Primer for Isolating ED Pathway-Related Gene

| Gene Source | Enzyme Gene | Forward | Reverse | Amplified Gene Base Sequence (Gene Code Region) |
|---|---|---|---|---|
| Zymomonas mobilis | zwf-edd | SEQ ID NO. 3 | SEQ ID NO. 4 | SEQ ID NO. 1 |
| Zymomonas mobilis | eda | SEQ ID NO. 5 | SEQ ID NO. 6 | SEQ ID NO. 2 |

TABLE 2

ED Pathway-Related Gene Expression Plasmid

| Gene Source | Enzyme Gene | Introduction Vector | Plasmid Name |
|---|---|---|---|
| Zymomonas mobilis | zwf-edd | pCRG5 | pCRG10 |
| Zymomonas mobilis | eda | pCRB214 | pCRG11 |

(3) Construction of Chromosome Integrated Strain

A DNA region necessary for markerless introduction of a gene into a chromosome of *Corynebacterium glutamicum* strain R was determined based on a sequence that was reported not to be essential far the growth of *Corynebacterium glutamicum* strain R [Appl Environ Microbiol. 2006 June; 71(6): 3369-3372] (SSI region). This DNA region was amplified by the PCR method. The DNA fragment thus obtained was introduced into a plasmid pCRA725 for markerless gene introduction [J Mol Microbiol Biotechnol. 2004; 8(4): 243-54/JP2006-124440A]. Incidentally, to pCRG12, a restriction enzyme site (unique site) for incorporating a gene in the SSI region by the inverse PCR method was introduced. The primer sequences used for isolation and the inverse PCR of the SSI regions and obtained vectors for chromosomal integration are shown in Table 3.

TABLE 3

Primer Sequence Used for Isolating SSI Region and Obtained Vectors for Chromosomal Integration

| Vectors for Chromosomal Integration | SSI Region | Forward | Reverse |
|---|---|---|---|
| pCRG12 | SSI 3-7 | SEQ ID NO. 9 | SEQ ID NO. 10 |
|  |  | SEQ ID NO. 11* | SEQ ID NO. 12* |
| pCRG13 | SSI 8-9 | SEQ ID NO. 13 | SEQ ID NO. 14 |

*Primer used in Inverse PCR method

From the ED pathway-related gene expression plasmids constructed as shown in Table 2, tac promoter fusion enzyme gene fragments were obtained and introduced into the above-described vectors for chromosomal integration, whereby plasmids pCRG14 and pCRG15 for chromosomal integration were constructed. Further, using pCRB215 [Appl Microbiol Biotechnol. 2016 June; 99(11): 4679-4689] and pCRB263 [WO2017/146241], a plasmid pCRG16 for chromosomal integration for the ldhA gene derived from *Lactobacillus delbrueckii* was constructed. Obtained plasmids for chromosomal integration are shown in Table 4.

TABLE 4

Plasmid for ED Pathway and D-Lactate Production-Related Gene Chromosomal Integration

| Gene Source | Gene | SSI Region | Plasmid for Chromosomal Integration |
|---|---|---|---|
| Zymomonas mobilis | zwf-edd | SSI 3-7 | pCRG14 |
| Zymomonas mobilis | eda | SSI 8-9 | pCRG15 |
| Lactobacillus delbrueckii | ldhA | SSI 4-7 | pCRG16 |

(4) Construction of Producing Strains by Chromosomal Gene Recombination

The plasmid pCRA725 for markerless chromosome gene introduction is a plasmid that cannot be replicated in *Corynebacterium glutamicum* R. In a case of a single crossover strain in which crossover occurs at the SSI region introduced into the plasmid pCRA725 and the homologous region on the chromosome, the strain exhibits the kanamycin resistance due to the expression of the kanamycin-resistant gene on pCRA725, and the lethality in a sucrose-containing medium due to the expression of the sacR-sacB gene of the *Bacillus subtilis*; in contrast, in a case of a double crossover strain, the strain exhibits the kanamycin sensitivity due to the loss of the kanamycin-resistant gene on pCRA725, and the viability in a sucrose-containing medium due to the loss of the sacR-sacB gene. A markerless chromosomal gene introduced strain, therefore, exhibits the kanamycin sensitivity and the viability in the sucrose-containing medium.

By the above-described method, the ED-pathway-related gene chromosome integrated strains were constructed by using the above-described plasmids for ED-pathway-related gene chromosomal integration. Coryneform bacteria CRZ14 [Appl Microbiol Biotechnol. 2015 February; 99(3): 1165*1172] and LPglc267 [Appl Microbiol Biotechnol. 2015 June; 99(11): 4679-4689] were used as host strains.

Further, a strain LHglc435 was constructed by using coryneform bacterium CRZ1 [J Mol Microbial Biotechnol. 2004; 8(4): 243-254] as a host, and using the following plasmids: plasmid pCRD109 for arabinose-utilizing gene (araBAD) chromosomal integration [Appl Microbiol Biotechnol. 2009 November; 85(1): 105-115]; plasmid pCKD108 for arabinose-transporter gene (araE) chromosomal integration [Appl Microbiol Biotechnol. 2009 November; 85(1): 105-115]; plasmid Xyl4-Xyl5 for xylose-utilizing gene (xylAB) chromosomal integration [Appl Microbiol Biotechnol. 2008 December; 81(4): 691*699]; plasmid Cell for cellobiose-utilizing gene (bglF(V317A) bglA) chromosomal integration [Appl Microbiol Biotechnol. 2008 December; 81(4): 691*699]; plasmid pCRD907 for gapA gene chromosomal integration [Appl Environ Microbiol. 2012 June; 78(12): 4447*4457]; plasmid pCRD913 for gpi gene chromosomal integration [Appl Environ Microbiol. 2012 June; 78(12): 4447-4467]; plasmid pCRB224 for tpi gene chromosomal integration [Appl Microbiol Biotechnol. 2013 August; 97(15): 6693*6703]; plasmid pCRB283 for tkt-tal gene chromosomal integration [WO2016/027870]; qsuB gene disruption plasmid pSKM26 [WO 2016/027870A1]; pobA gene disruption plasmid pCRA725*pohA/CG [WO2012/063860A1]; poxF gene disruption plasmid pCRA725*poxF/CG [WO2012/067174 A1]; qsuD gene disruption plasmid pSKM27 [WO2016/027870A1]; and aroK gene disruption plasmid pCRC329 [WO2016/027870 A1] This chromosomal gene recombination is outlined together in Tables 5 and 6.

TABLE 5

Construction of ED Pathway and D-Lactate Production-Related Gene introduced Strain by Chromosomal Gene Recombination

| Constructed Strain | Host Strain | Recombinant Plasmid | Chromosome Integrated Gene |
|---|---|---|---|
| CRZ14ED | CRZ14 | pCRG14, pCRG15 | zwf-edd, eda |
| LPglc267ED | LPglc267 | pCRG14, pCRG15 | zwf-edd, eda |
| LPglc349 | LPglc267 | pCRG16 | ldhA (L. delbrueckii) |
| LPglc349ED | LPglc267ED | pCRG16 | ldhA (L. delbrueckii) |
| LHglc435ED | LHglc435 | pCRG14, pCRG15 | zwf-edd, eda |

TABLE 6

Outline of Strain Construction by Chromosomal Gene Recombination

| Constructed Strain | Chromosome Integrated Gene | Disrupted Chromosomal Gene |
|---|---|---|
| CRZ14 | pgi, pfkA, gapAx2, tpi, pyk | ldhA, ppc |
| CRA14ED | pgi, pfkA, gapAx2, tpi, pyk, zwf-edd, eda | ldhA, ppc |
| LPglc267 | glk, pfkA, fba, gapAx2, tpi | ldhA, ppc |
| LPglc267ED | glk, pfkA, fba, gapAx2, tpi, zwf-edd, eda | ldhA, ppc |
| LPglc349 | glk, pfkA, fba, gapAx2, tpi, ldhA (L. delbrueckii) | ldhA, ppc |

TABLE 6-continued

Outline of Strain Construction by Chromosomal Gene Recombination

| Constructed Strain | Chromosome Integrated Gene | Disrupted Chromosomal Gene |
|---|---|---|
| LPglc349ED | glk, pfkA, fba, gapAx2, tpi, zwf-edd, eda, ldhA (L. delbrueckii) | ldhA, ppc |
| LHglc435 | Mixed Saccharide-Utilizing Gene** pgi, gapAx2, tpi | ldhA, qsuB, pobA, poxF, qsuD, aroK |
| LHglc435ED | Mixed Saccharide-Utilizing Gene** pgi, gapAx2, tpi, zwf-edd, eda | ldhA, qsuB, pobA, poxF, qsuD, aroK | x2: Indicating the number of genes introduced in chromosome
**Mixed saccharide-utilizing genes which are xylA gene (xylose isomerase), xylB gene (xylulokinase), araA gene (arabinose isomerase), araB gene (ribulokinase), and araD gene (ribulose-5-phosphate-3-epimerase) derived from Escherichia coli strain K-12; bglF (V317A) gene (β glucosidase) derived from Corynebacterium glutamicum strain R; bglA gene (6-phospho-β-glucosidase); and araE gene (arabinose transporter) derived from Corynebacterium glutamicum strain ATCC 31831, which are mixed saccharide-utilizing genes, are chromosomally integrated.

(5) Construction of Useful Material Producing Strains by Introducing Plasmid

Ethanol-producing strains were constructed by introducing pCRA723 [J Mol Microbiol Biotechnol. 2004; 8(4): 243-254] into the above-described chromosomal gene recombinant strains. Isobutanol-producing strains were constructed by introducing pCRB-BNC™ [Appl Environ Microbiol. 2012 February; 78(3): 865-875], pCRD926 and pCRD927 [Biotechnol Bioeng. 2013 November; 110(11): 2938-48] into the above-described chromosomal gene recombinant strains. Alanine-producing strains were constructed by introducing pCRD914 [Appl Environ Microbiol. 2012 June; 78(12): 4447-4457] into the above-described chromosomal gene recombinant strains. Shikimate-producing strains were constructed by introducing pCRB1-aroG/CG [WO2012/033112A1] and pSKM7 [WO2016/027870 A1] into the above-described chromosomal gene recombinant strains. The strains thus constructed are outlined in Table 7.

TABLE 7

Construction of Useful Material Producing Strain by Plasmid Introduction

| Constructed Strain | Host Strain | Introduced Plasmid | Product |
|---|---|---|---|
| ETH1 | CRZ14 | pCRA723 | Ethanol |
| ETH2 | CRZ14ED | | |
| IBU103 | CRZ14 | pCRB-BNC ™ | Isobutanol |
| IBU104 | CRZ14ED | pCRD926 pCRD927 | |
| ALA97 | LPglc267 | pCRD914 | Alanine |
| ALA98 | LPglc267ED | | |
| SHI2 | LHglc435 | pCRB1-aroG/CG | Shikimate |
| SHI3 | LHglc435ED | pSKM7 | |

Corynebacterium glutamicum ALA98 was deposited in Incorporated Administrative Agency National institute of Technology and Evaluation, NITE Patent Microorganisms Depositary (2-5-8-122 Kazusakamatari, Kisarazu-shi, Chiba 292-0818 Japan) as an international depositary authority (International deposit date: Apr. 17, 2018, Accession Number: NITE BP-02688 under the Budapest Treaty).

Example 2

Examination of Effect of ED Pathway Introduction with use of Ethanol-Producing *Corynebacterium glutamicum* Transformant Ethanol productivity under growth inhibiting conditions was studied by using ethanol-producing strains ETH1 and ETH2 constructed on the basis of a *Corynebacterium glutamicum* strain R (see Example 1 (Table 7)). Regarding strains to be subjected to evaluation, bacterial cells were prepared by culturing the same under aerobic conditions in a nutrient medium (obtained by dissolving the following in 1 liter of water: 2 g of urea, 2 g of yeast extract, 7 g of casamino acids, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 4.2 mg of $MnSO_4.H_2O$, 0.2 mg of biotin, and 0.2 mg of thiamin HCl) containing 4% of glucose and 5 ng/L of chloramphenicol. The bacterial cells obtained were suspended in a minimal medium (obtained by dissolving the following in 1 liter of water: 7 g of $(NH_4)_2SO_4$, 0.5 g of $KH_2PO_4$, 0.5 g of $K_2HPO_4$, 0.5 g of $MgSO_4.7H_2O$), 6 mg of $FeSO_4.7H_2O$, 4.2 mg of $MnSO_4.H_2O$, 0.2 mg of biotin, and 0.2 mg of thiamin) so that a concentration of 10 g (dried bacterial ceils) per liter was obtained, and glucose was added thereto, so that a production reaction was started. Aqueous solution of ammonium was added appropriately so that a reaction temperature of 33° C. and pH of 6.5 were maintained. The results of the production tests are shown in Table 8. The ED pathway-introduced strain (ETH2) exhibited noticeable improvement in the productivity-, as compared with the strain in which no ED pathway had been introduced (ETH1).

TABLE 8

Comparison of Ethanol Productivity in Presence/Absence of Introduced ED Pathway

| Strain | Production Rate (mmol/L/h) | Yield Relative to Saccharide (%) |
|---|---|---|
| ETH1 | 23.6 | 80 |
| ETH2 | 44.7 | 97 |

Example 3

Examination of Effect of ED Pathway Introduction with Use of Isobutanol-Producing *Corynebacterium Glutamicum* Transformant Isobutanol productivity under growth inhibiting conditions was studied by using isobutanol-producing strains IBU103 and IBU104 constructed cm the basis of a *Corynebacterium glutamicum* strain R (see Example 1 (Table 7)). Regarding strains to be subjected to evaluation, bacterial cells were prepared by culturing the same under aerobic conditions in a nutrient medium containing 4% of glucose, 50 ng/L of kanamycin, 5 ng/L of chloramphenicol, and 50 ng/L of zeocin. The bacterial cells obtained were suspended in a minimal medium so that a concentration of 20 g (dried bacterial cells) per liter was obtained, and glucose was added thereto, so that a production reaction was started. Aqueous solution of ammonium was added appropriately so that a reaction temperature of 33° C. and pH of 7.5 were maintained. The results of the production tests are shown in Table 9. The ED pathway introduced strain (IBU104) exhibited noticeable improvement in the productivity, as compared with the strain in which no ED pathway had been introduced (IBU103).

TABLE 9

Comparison of Isobutanol Productivity in Presence/Absence of Introduced ED Pathway

| Strain | Production Rate (mmol/L/h) | Yield Relative to Saccharide (%) |
|---|---|---|
| IBU103 | 15.9 | 59.8 |
| IBU104 | 23.3 | 63.4 |

Example 4

Examination of Effect of ED Pathway Introduction with use of D-Lactate Producing *Corynebacterium glutamicum* Transformant D-lactate productivity under growth inhibiting conditions was studied by using D-lactate-producing strains LPglc349 and LPglc349ED constructed on the basis of a *Corynebacterium glutamicum* strain R (see Example 1 (Table 6)). Regarding strains to be subjected to evaluation, bacterial cells were prepared by culturing the same under aerobic conditions in a nutrient medium containing 4% of glucose. The bacterial cells obtained were suspended in a minimal medium so that a concentration of 10 g (dried bacterial cells) per titer was obtained, and glucose was added thereto, so that a production reaction was started. Aqueous solution of ammonium was added appropriately so that a reaction temperature of 33° C. and pH of 7.0 were maintained. The results of the production tests are shown in Table 10. The ED pathway-introduced strain (LPglc349ED) exhibited noticeable improvement in the productivity, as compared with the strain in which no ED pathway had been introduced (LPglc349).

TABLE 10

Comparison of D-Lactate Productivity in Presence/Absence of Introduced ED Pathway

| Strain | Production Rate (mmol/L/h) | Yield Relative to Saccharide (%) |
|---|---|---|
| LPglc349 | 24.1 | 83 |
| LPglc349ED | 34.8 | 93 |

Example 5

Examination of Effect of ED Pathway Introduction with use of Alanine-Producing *Corynebacterium glutamicum* Transformant Alanine productivity under growth inhibiting conditions was studied by using alanine-producing strains ALA97 and ALA98 constructed on the basis of a *Corynebacterium glutamicum* strain R (see Example 1 (Table 7)). Regarding strains to be subjected to evaluation, bacterial cells were prepared by culturing the same under aerobic conditions in a nutrient medium containing 4% of glucose and 50 ng/L of kanamycin. The bacterial cells obtained were suspended in a minimal medium so that a concentration of 10 g (dried bacterial cells) per liter was obtained, and glucose was added thereto, so that a production reaction was started. Aqueous solution of ammonium was added appropriately so that a reaction temperature of 33° C. and pH of 7.0 were maintained. The results of the production tests are shown in Table 11. The ED pathway-introduced strain (ALA98) exhibited noticeable improvement in the productivity, as compared with the strain in which no ED pathway had been introduced (ALA97).

TABLE 11

Comparison of Alanine Productivity in Presence/Absence of Introduced ED Pathway

| Strain | Production Rate (mmol/L/h) | Yield Relative to Saccharide (%) |
|---|---|---|
| ALA97 | 26.3 | 80 |
| ALA98 | 45.0 | 86 |

Example 6

Examination of Effect of ED Pathway Introduction with use of Shikimate-Producing *Corynebacterium glutamicum* Transformant Alanine productivity under growth inhibiting conditions was studied by using alanine-producing strains SHI2 and SHI3 constructed on the basis of a *Corynebacterium glutamicum* strain R (see Example 1 (Table 7)). Regarding strains to be subjected to evaluation, bacterial cells were prepared by culturing the same under aerobic conditions in a nutrient medium containing 4% of glucose, 50 ng/L of kanamycin, 5 ng/L, of chloramphenicol 20 µg/ml of phenylalanine, 20 µg/ml of tyrosine, 20 µg/ml of tryptophan, and 10 µg/ml of p-aminobenzoate. The bacterial cells obtained were suspended in a minimal medium so that a concentration of 10 g (dried bacterial cells) per liter was obtained, and glucose was added thereto, so that a production reaction was started. Reaction was allowed to occur in a 1000 ml jar fermenter (manufactured by Able Corp., Type: BMJ1L) under the conditions of a reaction temperature of 33° C., an aeration amount of 0.25 L/min (air, 1 vvm), and dissolved oxygen concentration (DO) of 5% (assuming that the saturated dissolved oxygen concentration under the atmospheric pressure is 100%); aqueous solution of ammonium was added appropriately so that pH of 7.0 was maintained. The results of the production tests are shown in Table 12. The ED pathway-introduced strain (SHI3) exhibited noticeable improvement in the productivity, as compared with the strain in which no ED pathway had been introduced (SHI2).

TABLE 12

Comparison of Shikimate Productivity in Presence/Absence of Introduced ED Pathway

| Strain | Production Rate (mmol/L/h) | Yield Relative to Saccharide (%) |
|---|---|---|
| SHI2 | 0.22 | 16 |
| SHI3 | 0.29 | 18 |

INDUSTRIAL APPLICABILITY

The present disclosure is useful for producing useful organic compounds such as organic adds, amino acids, and alcohols.

SEQUENCE LISTING

The invention claimed is:

1. A transformant of a coryneform bacterium obtained by introducing genes encoding enzymes which constitute an Entner-Doudoroff pathway into the coryneform bacterium as a host,
wherein the transformant has a glycolytic pathway of the Entner-Doudoroff pathway and a glycolytic pathway of an Embden-Meyerhof-Parnas pathway,
wherein the coryneform bacterium is *Corynebacterium glutamicum*,
wherein the genes encoding enzymes which constitute the Entner-Doudoroff pathway comprise:
a gene encoding glucose-6-phosphate dehydrogenase;
a gene encoding 6-phosphogluconate dehydratase; and
a gene encoding 2-keto-3-deoxy-6-phosphogluconate aldolase,
wherein the transformant has increased production of an organic compound produced from pyruvate or phosphoenolpyruvate as an intermediate, relative to *Corynebacterium glutamicum* not having the Entner-Doudoroff pathway,
wherein the organic compound produced from pyruvate or phosphoenolpyruvate as an intermediate is selected from the group consisting of monocarboxylates, dicarboxylates, ketocarboxylates, hydroxycarboxylates, amino acids, monoalcohols, polyols, aromatic compounds, and vitamins.

2. The transformant according to claim 1,
wherein the glucose-6-phosphate dehydrogenase is an enzyme that can use oxidized nicotinamide dinucleotide as a coenzyme.

3. A method for producing an organic compound comprising the steps of:
causing the transformant according to claim 1 to react in a reaction solution in which at least one of factors necessary for growth is removed, or in a reaction solution under reduction conditions; and
collecting an organic compound in a reaction medium.

4. The method according to claim 3, wherein
the causing includes converting at least one saccharide selected from the group consisting of glucose, fructose, cellobiose, xylobiose, sucrose, lactose, maltose, dextrin, xylose, arabinose, galactose, mannose, and soluble starch into an organic compound with use of the transformant of the coryneform bacterium, in the reaction solution, and
the collecting includes collecting the organic compound from the reaction solution.

5. The method according to claim 3,
wherein the organic compound is either a compound produced from pyruvate as an intermediate, or a compound produced from phosphoenolpyruvate as an intermediate.

6. The method according to claim 3,
wherein the organic compound is at least one selected from the group consisting of monocarboxylates, dicarboxylates, ketocarboxylates, hydroxycarboxylates, amino acids, monoalcohols, polyols, aromatic compounds, and vitamins.

7. The transformant according to claim 1,
wherein the gene encoding glucose-6-phosphate dehydrogenase is a glucose-6-phosphate -1-dehydrogenase gene zwf of *Zymomonas mobilis*;
the gene encoding 6-phosphogluconate dehydratase is a 6-phosphogluconate dehydrogenase gene edd of *Zymomonas mobilis*; and/or
the gene encoding 2-keto-3-deoxy-6-phosphogluconate aldolase is a 6-phosphogluconate dehydratase gene eda of *Zymomonas mobilis*.

8. The transformant according to claim 7,
wherein said transformant comprises the nucleotide sequence of SEQ ID NO: 1.

9. The transformant according to claim 7,
wherein said transformant comprises the nucleotide sequence of SEQ ID NO: 2.

10. The transformant according to claim 1,
wherein the organic compound produced from pyruvate or phosphoenolpyruvate as an intermediate is selected from the group consisting of L-lactate, D-lactate, acetate, 3-hydroxypropionate, acrylate, succinate, fumarate, malate, oxaloacetate, citrate, cis-aconitate, itaconate, isocitrate, 2-oxoglutarate, 2-hydroxyisovalerate, ethanol, 1,3-propanediol, glycerol, butanol, isobutanol, 1,4-butanediol, xylitol, sorbitol, valine, leucine, alanine, aspartate, lysine, isoleucine, threonine, shikimate, protocatechuate, catechol, 4-hydroxybenzoate, phenol, tyrosine, phenyl alanine, and tryptophan.

11. The transformant according to claim 1,
wherein the organic compound produced from pyruvate or phosphoenolpyruvate as an intermediate is selected from the group consisting of ethanol, isobutanol, D-lactate, alanine, and shikimate.

* * * * *